United States Patent [19]
Payne

[11] Patent Number: 5,962,793
[45] Date of Patent: Oct. 5, 1999

[54] COMPACT FEED PELLET DURABILITY TESTER

[75] Inventor: John David Payne, Hants, United Kingdom

[73] Assignee: Borregaard UK Limited, Warrington, United Kingdom

[21] Appl. No.: 09/003,146

[22] Filed: Jan. 6, 1998

[30] Foreign Application Priority Data

Jan. 7, 1997 [GB] United Kingdom ............ 9700180

[51] Int. Cl.$^6$ ................................................. G01F 13/00
[52] U.S. Cl. ................................................. 73/861.41; 73/866
[58] Field of Search .................................. 73/861.41, 866

[56] References Cited

U.S. PATENT DOCUMENTS

| | | | |
|---|---|---|---|
| 4,143,539 | 3/1979 | Baillie | 73/866 |
| 4,582,254 | 4/1986 | Rotolico et al. | 239/80 |
| 5,309,773 | 5/1994 | Tokoyama | 73/863.01 |

FOREIGN PATENT DOCUMENTS

| | | |
|---|---|---|
| 0085507 | 8/1983 | European Pat. Off. . |
| 0608196 | 7/1994 | European Pat. Off. . |
| 2181559 | 4/1987 | United Kingdom . |

*Primary Examiner*—Max Noori
*Attorney, Agent, or Firm*—Nixon & Vanderhye

[57] ABSTRACT

A compact pellet tester for testing the durability of animal feed pellets. The tester comprises a perforated hopper into which a high velocity stream of air is directed upward to agitate the pellets to measure the amount of material or fines which break off during testing.

16 Claims, 4 Drawing Sheets

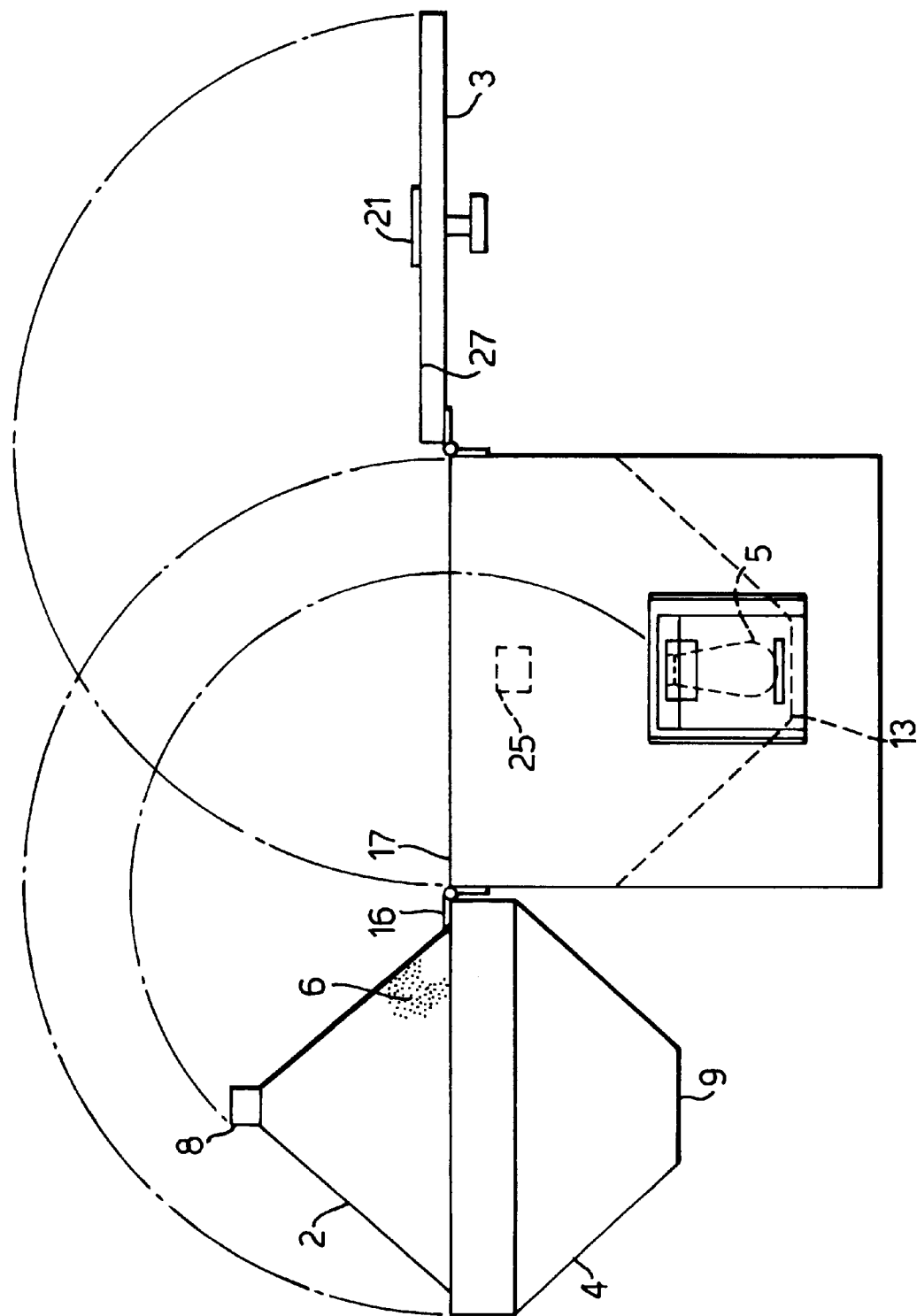

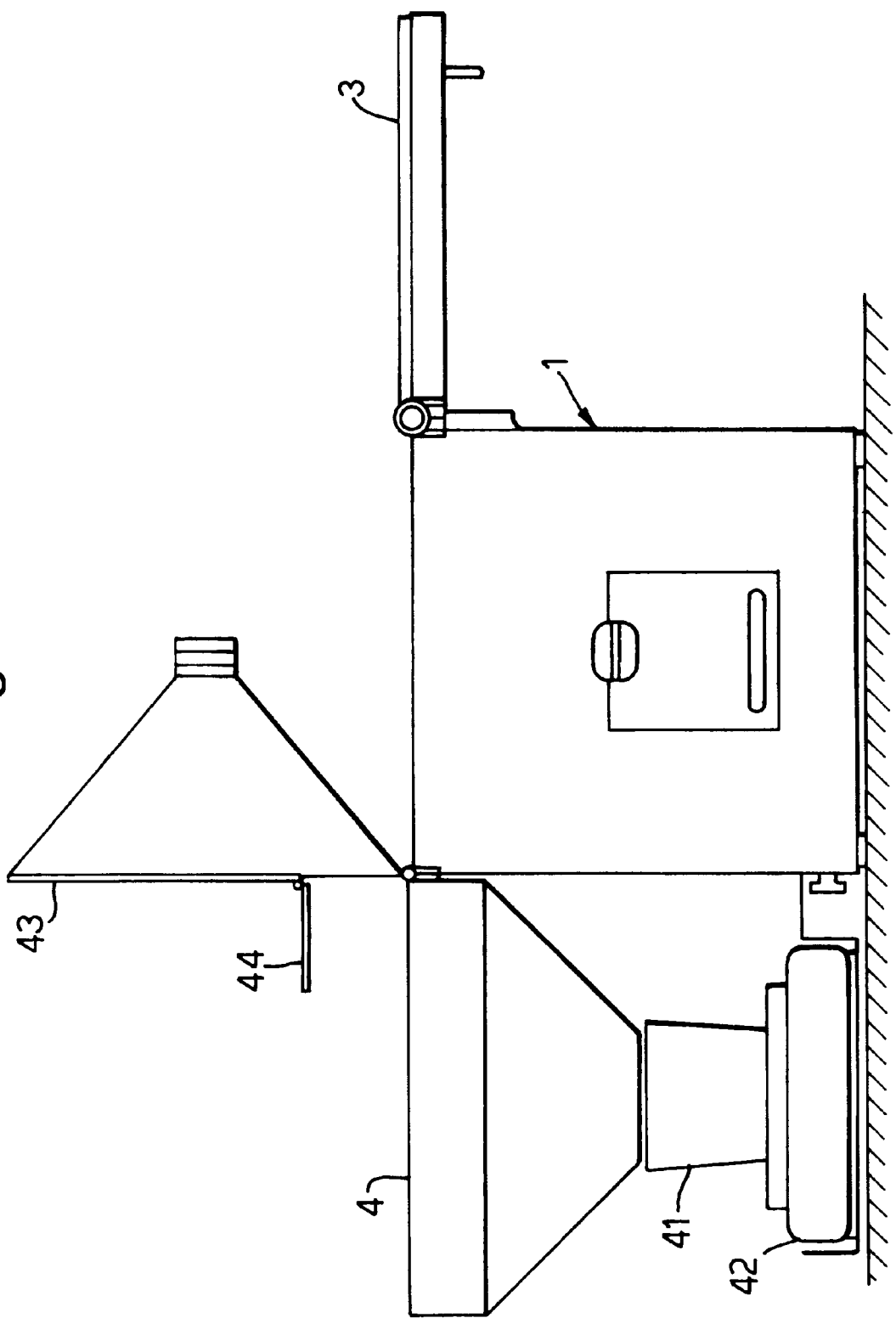

COMPACT FEED PELLET DURABILITY TESTER

FIELD OF THE INVENTION

The present invention relates to devices for measuring the durability of feed pellets.

In order to provide a convenient means of transporting animal feed from the feed mill to the end user (eg. form), the feed is formed into pellets. These pellets are typically anything from a couple of millimeters up to 20 millimeters in diameter. However, in forming these pellets, it is important to produce a pellet which will remain intact during distribution from the feed mill to the animal being fed whilst still being suitable for consumption and digestion by the animal. There is therefore a fine balance between providing a pellet which is indestructible during transit but indigestible by the animal and one which is easily eaten and digested by the animal but is likely to break up during transit.

It is therefore desirable to be able to monitor the durability of the pellets.

PRIOR ART

Various devices have been proposed for providing measures of the durability of pellets. EP-B-0,085,507 describes an apparatus in which pellets are repeatedly fed through a section of tubing to simulate the treatment which would occur during transportation from the feed mill to the end user. GB-B-2,181,559 describes an alternative feed pellet durability testing apparatus in which the feed pellets are dropped into a hopper having perforated sides and a jet of air is blasted upwards from the bottom of the hopper to agitate the pellets. Any pieces which break off pass through the perforated sides of the hopper and pass out at the bottom of the machine carried along with the airflow.

Both the above described devices are designed for use on a production line, for continuous testing of the quality of the feed pellets being produced. However, these devices are large and bulky and are thus not easily moved for testing pellets in a different location. This means that if testing of the pellets is to be carried out in more than one location within the factory or outside of the factory (eg. at a distribution centre or at the receiving farm), it is necessary to have dedicated testers at each location.

OBJECT OF THE INVENTION

It is therefore desirable to provide a tester which is compact enough to be moved from one location to the other and which requires a minimum of setting up and dismantling between each relocation.

SUMMARY OF THE INVENTION

Therefore, according to the present invention there is provided a pellet durability tester comprising:
- a hopper into which the pellets are inserted for testing, having at least a portion of its sides perforated to allow fines to pass out of the hopper;
- a nozzle through which a stream of compressed air enters the base of the hopper to agitate the pellets, in use; and
- a lid provided over the top of the hopper, to prevent, in use, the fines escaping from the tester.

The tester preferably includes a blow fan timer which, when activated, operates the blower for a preset period of time. This provides a standardised testing period. This preset period of time is preferably 30 seconds. The hopper is preferably hinged at one side of the tester to allow it to pivot out of the body of the tester to tip the contents of the hopper into another container for weighing. The lid is also preferably hinged to the body of the tester so that it can be pivoted away from the top of the hopper to allow the hopper to be emptied. The lid preferably incorporates a filter comprising on air permeable filter pad or sheet to allow air to escape through to the lid.

The tester is preferably provided with a hood positioned over the filter. The hood is preferably hingedly attached to the body of the tester to allow it to be pivoted away from the top of the filter, to allow the filter and hopper to be moved. The hood is preferably provided in the form of a truncated pyramid or cone such that when the hopper is pivoted through 180° it forms a funnel portion into which the hopper can be tipped to provide easier collection of the tested pellets. For simplicity of operation, it is preferable if the hopper and the hood pivot along the same axis such that the filter is simply pivoted directly over the top of the hopper.

The lid may also be pivotably attached to the upper edge of the tester, preferably on a different side to the hopper and the hood.

The provision of the lid over the top of the hopper allows the tester to be used in any environment, as the filter prevents any of the fines escaping from the tester. This is important where the tester is being used in an environment where the production of large amounts of dust would be unacceptable, such as in an office. Furthermore, with increasingly stricter regulations on dust emissions being introduced, it is important that the tester produces only a minimal amount of dust pollution.

Locating the filter at the top of the tester means that fewer fines get caught in the filter, increasing the amount of time between filter replacement and/or cleaning.

The filter is preferably supported above and below by a rigid support. This support may be in the form of a perforated plate, cross-members or the like, so as to support the filter without unnecessary impeding the air flow. Alternatively, the lower filter support may be provided on the top of the hopper. In order to allow the pellets to be inserted and removed, some or all of such a filter support may be hinged on the hopper, so as to provide an opening flap.

The filter may include a shield portion comprised of a thin solid disc, a few (approximately 5) centimeters in diameter in the centre of its underside. The shield portion, which is preferably impervious to air, covers part of the filter above the nozzle. The disc deflects pellets and fines projected upward by the air jet, preventing the fines being lodged in the filter. The action of the pellets hitting the disc and the rest of the filter causes vibration in the filter, dislodging any fines which may be lodged in the filter.

The filter may be used several times before being replaced. Alternatively, the filter may be discarded and replaced after each test. By using a new filter every time a test is conducted, the starting conditions are always the same and thus greater continuity between tests can be achieved.

The large upper area and overall volume of the hopper allows testing of all sizes of pellets currently available without the need to switch to different hoppers. By avoiding the need to dry the pellets in the tester (by running the blower at a slower speed) as is commonly done in online testers, it is only necessary to provide a single speed air blower, thus providing much simpler drive control of the blower motor. This further simplifies the construction of the tester and hence reduces cost. The power supply to the motor is preferably stabilized. By providing voltage stabilising circuitry in the tester itself, the motor always operates at the same speed. This helps to avoid variations in conditions from one test to the next irrespective of the quality of electrical supply to the tester. The speed of the blower motor may however be adjustable to compensate for variations in speed of the motor, and hence the pressure and velocity of the air jet, with time, eg. due to aging of the motor and/or clogging of the filter. The tester may also be provided with a pressure transducer to monitor the pressure in the testing chamber, to aid in the above mentioned calibration and also to monitor the increase in pressure with time as a result of back-pressure due to clogging of the filter.

The compact construction of the tester allows it to be carried around whilst still being capable of testing a large range of pellet sizes.

BRIEF DESCRIPTION OF THE DRAWINGS

The present invention will be more clearly understood from the following description, given by way of example only, with reference to the accompanying drawings in which:

FIG. 3 is a schematic cross-section of the tester from another side, showing the pivoting members in their open condition; and FIG. 4 is a view of an alternative arrangement of the tester according to the present invention.

DETAILED DESCRIPTION OF THE PREFERRED MODE

Figure 1:
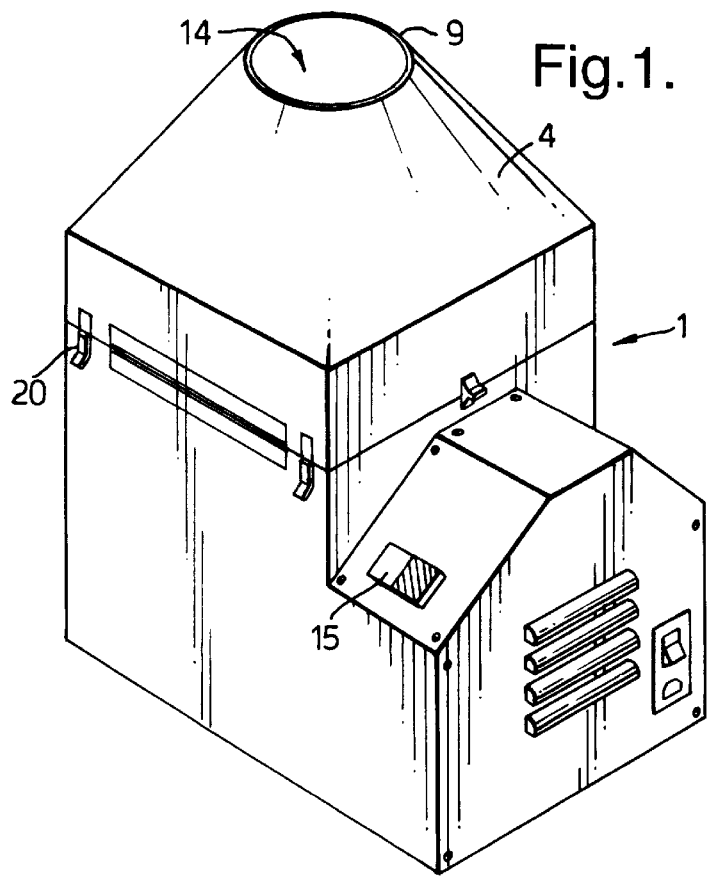
FIGS. 1 and 1A show two different views of a tester according to the present invention.
Figure 1A:
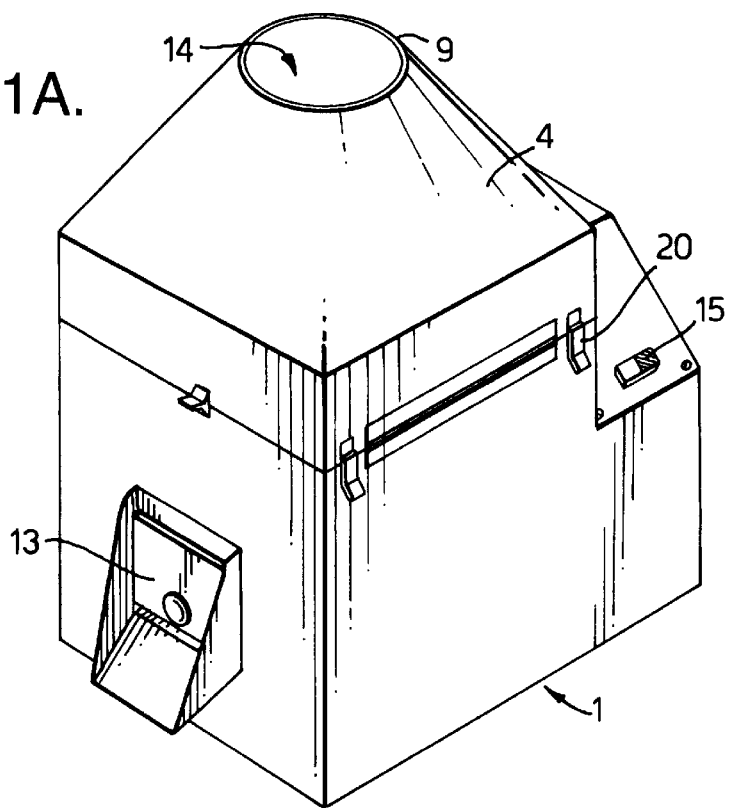
Figure 2:
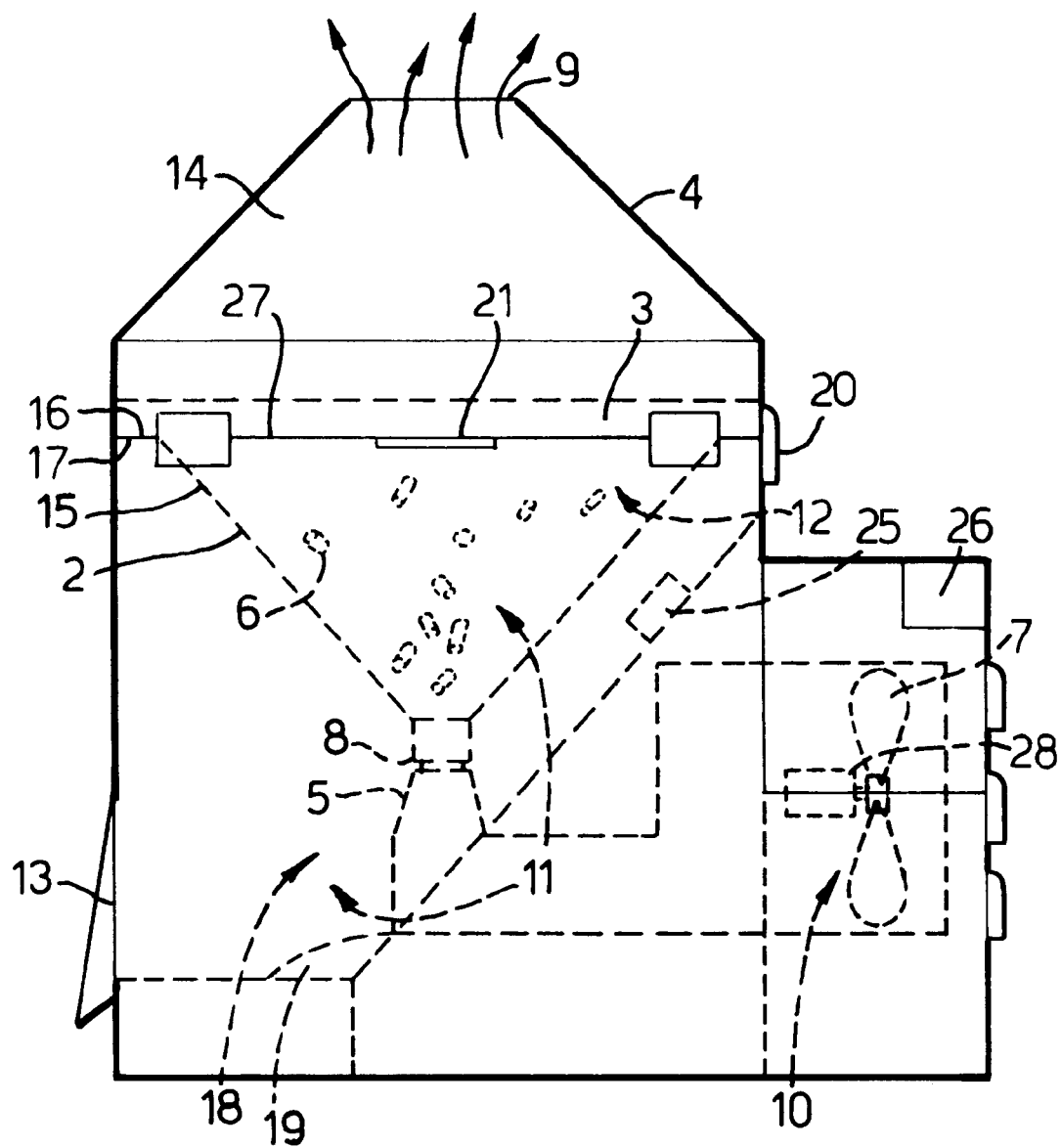
FIG. 2 is a schematic cross-section of a tester from one side.

The tester 1 is provided in a housing which is divided into two parts, a pumping chamber 10 and a testing chamber 11. The pumping chamber 10 contains a motorised blower unit 7 for pressurizing the testing chamber 11. The pumping chamber is connected to the testing chamber via a nozzle 5 which converts the pressure head inside the pumping chamber into a velocity head.

The testing chamber 11 has an open top into which is inserted a hopper 2. The hopper has a generally conical or pyramidal shape with a rim 16 at the larger end. The rim 16 rests on the upper edge 17 of the body of the tester 1 with the body of the hopper 2 contained within the testing chamber 11. The hopper is hinged at one edge to the edge of the tester body so that it can be swung out of the body. The sides of the hopper are perforated to allow fines to pass into the fine collecting chamber 18. The bottom 8 of the hopper is provided with a flat portion which is perforated and which sits in abutment with the nozzle opening. Alternatively the bottom 8 of the hopper may be provided with a hole which is covered by a fine mesh.

A filter 3 is provided over the hopper to define a tumbling chamber 12 between the hopper and the filter. The filter 3 comprises a substantially flat rigid body with a sheet or pad of filter material such as foam provided therein. The filter is also hinged to the body of the tester, on the opposite side of the hopper, so that the filter can be swung out of the way of the hopper (see FIG. 3). The filter sheet or pad is supported from above and below by a rigid perforated plate 27.

In an alternative construction, the lower filter support 43, 44 is provided on the top of the hopper (see FIG. 4). This reduced the number of surfaces which need to be sealed by the filter frame and this minimises the possibility of leaks which can alter the pressure and hence accuracy of the device. The filter support comprises a flapped portion 44 which can be hinged open to allow the pellets to be inserted and removed from the hopper.

In the centre of the underside of the filter 3 is provided a rigid disc 21 of approximately 5 cm diameter. The disc 21 shields the portion of the filter directly above the nozzle 5 from the air jet. This prevents fines being blasted into the mesh of the filter pad and becoming lodged there, or rupturing the filter sheet where used.

As the pellets and the fines hit the underside of the filter 3, both on the disc 21 and the rest of the filter pad, they cause vibration of the filter which loosens any fines caught there. This helps to minimise any inconsistency between measurements due to variations in air flow and pressure and allows the period between cleaning and replacing the filter to be extended.

Rubber strips or the like are provided between the filter and the tester body or between the filter and the hopper and between the hopper and the tester body to form a seal. Thus the testing chamber is sealed except for the inlet nozzle and the outlet through the filter.

The walls of the hopper divide the testing chamber 11 into two regions: the tumbling chamber 12, is provided above the hopper; and the fine collection chamber 18 provided below the hopper.

Hingedly attached to the upper part of the testing chamber 11 is a hood 4. The hood 4 has the shape of a truncated cone or pyramid with a hole 9 provided at the upper part. This hole 9 provides two functions. During the tumbling phase of operation, the air from the nozzle passes into the tumbling chamber 12 and through the filter 3 into the volume 14 contained within the hood. The hole therefore provides an exit vent or chimney through which the air can escape. The second function of the hole is that once tumbling is complete and the pellets are being removed from the hopper, the hood is pivoted through 180° as shown in FIG. 3 such that the hole 9 is now facing downwards. The hopper and its contents 6 can be similarly pivoted about the same axis such that the upper portion of the hopper comes to rest on top of the hood portion, tipping the tested pellets 6 into the hood 4, such that they are funnelled out of the hole 9 in the hood into a collection container 41 provided below.

In order to test a sample of pellets 6, the user initially weighs the pellets to establish their starting weight. The hood 4 and filter 3 are then pivoted through 180°, in opposite senses, to expose the hopper. The pellets are then tipped into the hopper and the filter is returned to its position over the top of the hopper. The hood is then similarly returned to its position over the top of the filter and locked down, by locks 20, in position. The user then presses the start button 15 to initiate the test sequence. The blower forces air from the blower chamber into the nozzle, providing a high velocity jet of air directed vertically upward into the pile of test pellets 6 lying at the bottom of the hopper. The air throws the pellets into the air and against the filter and out to the side where they fall against the sides of the hopper. The pellets then slip down the sides of the hopper back to the bottom again and into the air stream where they are again thrown upwards in the air jet. This repeated cascading of the pellets in the chamber results in repeated collisions between the pellets and the walls of the tumbling chamber causing small parts of the pellets, called fines 19, to break off. The perforations provided in the sides of the hopper allow the fines to drop through into the fine collecting chamber 18 of the testing chamber 11. As air is blown into the tumbling chamber the pressure within increases, causing a flow of air through the filter pad into the hollow part of the hood and out through the chimney at the top. The filter pad prevents any fines from passing out of the tester. Any fines in the tumbling chamber will ultimately fall through the hopper perforations and collect in the fine collection chamber. The fines can then be emptied at a later time through the door 13 provided on the side of the tester. The door 13 is substantially air-tight to prevent air escaping during testing.

The controller for the tester will turn off the blower after a predetermined test period. It is important to have a fixed test period to ensure consistency of test results. Typically a test period of about 30 seconds is satisfactory to provide appropriate test results. However, there may be reasons for having an extended test period, for example, if the pellets are particularly durable and require a considerable amount of tumbling before an appreciable amount of material breaks off. Such extended test periods can be simply provided by running the tester for two or more normal (30 s) test periods. In order to maintain continuity of test results throughout the life of the tester, calibration can be carried out periodically. As the blower motor 28 ages, it may change its speed and efficiency characteristics. To counter this the tester may be provided with means to carry out small adjustments to the speed of the motor. In order to monitor performance of the blower, a pressure sensor 25 is provided in the testing chamber 11. This measures the pressure in the chamber 11 to allow calibration of the blower to a set pressure. This sensor can also be used to monitor an increase in pressure due to the build up of filtered material in the filter. By monitoring this pressure, it can be ascertained when it is necessary to clean or replace the filter.

Once the controller has shut down the blower and no further tumbling period is required, the user releases and opens the hood. The filter is also then pivoted out of position and finally the hopper is pivoted out of the body of the tester so that the remaining pellets are tipped into the hood. The pellets drop into the hood and run down the angled sides and out of the bottom of the hole 9. They are then collected in a collection container 41 and reweighed. Alternatively, they may be tipped directly onto the weighing device 42. The end weight of the pellets provides an indication of the durability of the pellets. The user normally starts with 100 grams of pellets prior to testing. For example, during testing 8 grams in weight is lost as a result of fines breaking off the pellets, such that only 92 grams remains when the pellets are weighed at the end of the testing procedure. The end weight provides an indication of the durability, or a durability value, eg. 92.

The dimensions of the hopper opening at the top of the tester is about 280 mm×280 mm which allows the full range of feed pellets to be accommodated in the hopper whilst providing a tester of a manageable size about 380 mm(l)× 280 mm(w)×430 mm(h).

I claim:

1. A pellet durability tester comprising:
   a tester housing having an upper edge;
   a hopper in said tester housing, said hopper having a bottom portion, a top portion and an interior;
   a lid to said hopper;
   side walls to the hopper;
   means defining perforations on at least a portion of said side walls for allowing fines to pass out of the hopper;
   a nozzle opening into said hopper in said bottom portion thereof and oriented to point towards the internal portion of the hopper; and
   means generating a flow of air to said nozzle for discharge therefrom into said hopper;
   said lid being movable between a first lid position, above the top portion of the hopper and a second lid position where the lid is clear of the top portion of the hoppers and
   hinge means having a hinge axis, said hinge means hingedly securing the hopper to the housing and permitting rotation of the hopper about said hinge axis through 180° between a first position in which the hopper is substantially contained within the tester housing and a second position in which the hopper is removed from said interior of the tester housing and is inverted.

2. A pellet durability tester according to claim 1 wherein said side walls of said hopper converge downwardly toward one another and toward said hopper bottom portion and said nozzle opening.

3. A pellet durability tester according to claim 1, wherein the lid comprises a filter to allow air to pass through said filter but preventing the pellets or parts thereof from passing through said filter.

4. A pellet durability tester according to claim 3 wherein the filter is chosen from the group consisting of a pad and a sheet.

5. A pellet durability tester according to claim 3, wherein the filter includes a substantially flat, rigid shield means, the shield means being positioned above the nozzle, when the lid is in the first lid position.

6. A pellet durability tester according to claim 3, wherein the top portion of the hopper comprises an air permeable filter support member.

7. A pellet durability tester according to claim 6, wherein the filter support member comprises flap means and flap hinge means having a flap hinge axis and hingedly attaching the filter support member to the hopper and for pivoting about said flap hinge axis, between a first position in which the filter support member closes the top portion of the hopper and a second position in which the flap is pivoted away from the top portion of the hopper defining an opening to allow removal and insertion of pellets.

8. A pellet durability tester according to claim 1, further including a hood provided over the top portion of the tester, the hood having:
   a top portion,
   a lower edge portion and
   side portions, the side portions defining a volume above the lid and
   the top portion defining a hole in the hood.

9. A pellet durability tester according to claim 8, further comprising hood hinge means at the lower edge portion of the hood, wherein the hood hinge means is hingedly attached to the upper edge of the tester housing and is pivotable through 180° from a first position above the tester housing to a second position in which the hood is inverted.

10. A pellet durability tester according to claim 9, wherein the hood is hinged along the same axis and along the same edge of the tester as is the hopper such that when both the hood and the hopper are rotated, the hopper is positioned over the hood.

11. A pellet durability tester according to claim 1, further comprising a single speed motor for driving said means generating a flow of air.

12. A pellet durability tester according to claim 11, further comprising voltage stabilisation means providing a stabilised voltage supply to the motor.

13. A pellet durability tester according to claim 12, further comprising controller means to control the motor to operate for a predetermined period and then stop.

14. A pellet durability tester according to claim 13, wherein said predetermined period is 30 seconds.

15. A pellet durability tester according to claim 1, further comprising a pressure sensor for monitoring the air pressure in the tester housing.

16. A pellet durability tester according to claim 2 wherein said perforations lie in communication with a fines collection chamber within said tester housing.

* * * * *